United States Patent [19]
Kunihiro et al.

[11] Patent Number: 5,834,028
[45] Date of Patent: Nov. 10, 1998

[54] SOLUBLE THROMBOMODULIN-CONTAINING COMPOSITION

[75] Inventors: Yasuyuki Kunihiro; Ryo Tanaka; Seishichi Hata; Shigeharu Suzuki; Yumio Kudoh, all of Tokyo, Japan

[73] Assignee: Mochida Pharmaceutical Co., Ltd., Tokyo, Japan

[21] Appl. No.: 505,337

[22] PCT Filed: Dec. 16, 1994

[86] PCT No.: PCT/JP94/02128

§ 371 Date: Aug. 17, 1995

§ 102(e) Date: Aug. 17, 1995

[87] PCT Pub. No.: WO95/16460

PCT Pub. Date: Jun. 22, 1995

[30] Foreign Application Priority Data

Dec. 17, 1993 [JP] Japan ................................. 5-318405

[51] Int. Cl.$^6$ .......................... A61K 35/22; A61K 38/54; A61K 35/14
[52] U.S. Cl. .......................... 424/545; 424/94.3; 530/381
[58] Field of Search .......................... 530/381; 424/545, 424/94.3

[56] References Cited

U.S. PATENT DOCUMENTS

| | | | |
|---|---|---|---|
| 5,202,421 | 4/1993 | Kunihiro et al. | 530/350 |
| 5,300,490 | 4/1994 | Kunihiro et al. | |

FOREIGN PATENT DOCUMENTS

| | | |
|---|---|---|
| 0217379 | 4/1987 | European Pat. Off. . |
| 0312598 | 4/1989 | European Pat. Off. . |
| 0445304 | 9/1991 | European Pat. Off. . |
| 0489180 | 6/1992 | European Pat. Off. . |
| 64-6219 | 1/1989 | Japan . |
| 2-255699 | 10/1990 | Japan . |
| 3-218399 | 9/1991 | Japan . |
| 5-58899 | 3/1993 | Japan . |
| WO91/04276 | 4/1991 | WIPO . |
| WO92/00325 | 1/1992 | WIPO . |
| WO93/15755 | 8/1993 | WIPO . |

OTHER PUBLICATIONS

Mohri et al, American Journal of Hematology, 45: 298–303 (1994).

Ketchum, et al., Menaquinol–nitrate oxidoreductase of Bacillus halodenitrificans, J Bacteriol, 173 (8) p. 2498–2505, see Abstract, Apr. 1991.

Hoover J. et al. Remington's Pharmaceutical Sciences 18th edition; Philadelphia College of Pharmacy and Science, 1990.

Primary Examiner—Donald E. Adams
Assistant Examiner—Hankyel T. Park
Attorney, Agent, or Firm—Birch, Stewart, Kolasch & Birch, LLP

[57] ABSTRACT

The present invention is directed to a soluble thrombomodulin-containing composition comprising at least one molecular species of soluble thrombomodulin, and at least one member selected from the group consisting of maltose, lactose, sucrose, arginine and a salt thereof, and a nonionic surface-active agent; and a production method therefor; as well as a stabilizing agent; a stabilization method; an anti-adsorption agent; and an anti-adsorption method for the soluble thrombomodulin. The present invention provides a soluble thrombomodulin-containing lyophilized preparation which is useful as a prophylactic or therapeutic agent for diseases associated with abnormalities in blood coagulation, and which is stable for a prolonged period of time and would not become adsorbed onto the container; and a production method therefor; as well as a stabilization agent; a stabilization method; an anti-adsorption agent; and an anti-adsorption method for the soluble thrombomodulin.

14 Claims, No Drawings

SOLUBLE THROMBOMODULIN-CONTAINING COMPOSITION

FIELD OF THE INVENTION

This invention relates to a composition containing as its critical components at least one species of soluble thrombomodulin and at least one member selected from maltose, lactose, sucrose, and arginine and a salt thereof; and a method for producing such composition.

This invention also relates to a composition containing as its critical components at least one species of soluble thrombomodulin and a nonionic surface-active agent; and a method for producing such composition.

Furthermore, this invention also relates to a composition containing as its critical components at least one species of soluble thrombomodulin; at least one member selected from maltose, lactose, sucrose, and arginine and a salt thereof; and a nonionic surface-active agent; and a method for producing such composition.

Still further, this invention relates to a stabilizing agent for a soluble thrombomodulin containing at least one member selected from maltose, lactose, sucrose, and arginine and a salt thereof.

Still further, this invention relates to a method for stabilizing a soluble thrombomodulin comprising the step of adding at least one member selected from maltose, lactose, sucrose, and arginine and a salt thereof to the soluble thrombomodulin.

Still further, this invention relates to an anti-adsorption agent for a soluble thrombomodulin containing a nonionic surface-active agent.

Still further, this invention relates to a method for preventing adsorption of a soluble thrombomodulin comprising the step of adding a nonionic surface-active agent to the soluble thrombomodulin.

BACKGROUND ART

Thrombomodulin is a protein found at vascular endotherial cell surface that has a unique nature of converting thrombin from a coagulant enzyme to an anti-coagulant enzyme, and it was reported in 1981 (Esmon et al., Proc. Natl. Acad. Sci. USA, 78, 2249–2254, 1981). In the subsequent report, Esmon et al. reported that they have succeeded in isolating the thrombomodulin from rabbit lung tissue (Esmon et al., J. Biol. Chem., 257(2), 859–864, 1982). The entire DNA sequence and the amino acid sequence of human thrombomodulin were then reported (EMBO J., 6, 1891–1897, 1987; Biochemistry, 26(14), 4350–4357, 1987), and various studies have been conducted to reveal the functions of different domains of the thrombomodulin. Today, it is conceived that thrombomodulin binds with thrombin to form a thrombin-thrombomodulin complex, and the blood coagulation activity of the thrombin is thereby lost; and in turn, the resulting thrombin-thrombomodulin complex activates protein C to induce anti-coagulation activity. In other words, the thrombomodulin may simultaneously induce the blood coagulation inhibitory action and the fibrinolytic action, and clinical application of thrombomodulin is highly awaited.

Conventional therapeutic agents that have been used for diseases related to blood coagulation activity disorders include agents having an anti-coagulation activity such as antithrombin III and heparin as well as agents having a thrombolytic activity such as urokinase, streptokinase, and tissue plasminogen activator. These agents, however, suffer from side effects such as tendency to hemorrhages, and their actions are either inclined to blood coagulation or thrombolysis. In view of such situation, a great expectation is held for the clinical application of a substance that may simultaneously have the anti-coagulation activity and the thrombolytic activity such as thrombomodulin, and a thrombomodulin-like substance that may have the thrombomodulin activity, i.e. both the affinity for thrombin and the protein C-activating activity.

Human thrombomodulin has a low solubility, and when the human thrombomodulin is used for a medicament, such low solubility results in the difficulty of purification as well as the difficulty in producing the preparation. More illustratively, thrombomodulin is a membrane-bound protein comprising five domains, that is, amino terminal domain, domain of EGF-like structure, domain of O-glycosilation site, transmembrane domain, and cytoplasmic domain, and the thrombomodulin of full length amino acid sequence would require a solubilizing agent upon its purification or production into a preparation. Therefore, there have been a strong demand for a thrombomodulin-like substance that may have an increased solubility (which is hereinafter referred to as a soluble thrombomodulin). In consideration of antigenicity and other safety requirements, a natural human thrombomodulin, such as natural human urine thrombomodulin is most desirable. Of the soluble thrombomodulins, typical genetically engineered soluble thrombomodulins are thrombomodulins having transmembrane and cytoplasmic domains deleted therefrom such as Japanese Patent Application Laid-Open Nos. 1(1989)-6219, 2(1990)-255699, 3(1991)-133380, 3(1991)-259084, and 4(1992)-210700; PCT Application Japanese Language Laid-Open Nos. 3(1991)-503757 and 4(1992)-505554, EP474273, WO91/04276, WO91/05803, WO91/15514, WO92/00325, WO92/03149, and WO93/15755; and Doi et al., the Pharmaceutical Society of Japan, 113rd Meeting, Lecture Summaries 3, Lecture No. 30EM14-1, 1993. Typical natural thrombomodulins include human urine soluble thrombomodulins as disclosed in japanese Patent Application Laid-Open Nos. 63(1988)-30423, 63(1988)-146898, 3(1991)-86900, and 3(1991)-218399; Ishii et al., J. Clin. Invest., 76, 2178–2181, 1985; Hiramoto et al., the Pharmaceutical Society of Japan, 108th Meeting, Lecture Summaries, Lecture No. 6F05 11-1, 1988; Yatani et al., Vessels (Ketsueki to Myakukan), 20, 197–200, 1989; and Yamamoto et al., J. Biochem., 113, 433–440, 1993.

With regard to the genetically engeneered soluble thrombomodulins, Japanese Patent Application Laid-Open No. 1(1989)-6219 discloses a soluble thrombomodulin comprising at least the amino acid sequence of from 345th to 462nd amino acid residues from the amino terminal; Japanese Patent Application Laid-Open No. 2(1990)-255699 discloses a soluble thrombomodulin comprising 115 amino acid residues; Japanese Patent Application Laid-Open No. 3(1991)-133380 discloses a soluble thrombomodulin comprising at least the amino acid sequence of from 1st to 497th amino acid residues from the amino terminal; Japanese Patent Application Laid-Open No. 3(1991)-259084 discloses a soluble thrombomodulin comprising 468 amino acid residues; Japanese Patent Application Laid-Open No. 4(1992)-210700 discloses a soluble thrombomodulin that is not modified with sulfated glycosaminoglican; PCT Application Japanese Language Laid-Open No. 3(1991)-503757 discloses a soluble thrombomodulin that may contain a part of the amino acid sequence of human tissue plasminogen activator; PCT Application Japanese Language Laid-Open No. 4(1992)-505554 discloses a soluble thrombomodulin that may contain a part of amino acid sequence of human tissue plasminogen activator; EP474273 discloses a soluble thrombomodulin containing the thrombin-binding site comprising 19 amino acid residues and the protein C-activation site; WO91/04276 discloses a soluble thrombomodulin having a sugar chain containing chondroitin and/or chondroitin sulfate; WO91/05803 discloses a soluble thrombomodulin that is modified with sulfated glycosaminoglican; WO91/15514 discloses a soluble thrombomodulin wherein methionine is substituted with another amino acid to prevent oxidation. WO92/00325 discloses a recombinant human urine soluble thrombomodulin and mutants thereof; WO92/03149 discloses a soluble thrombomodulin wherein sugar chain at the domain of O-glycosilation site is modified, and a soluble thrombomodulin having the domain of O-glycosilation site deleted therefrom; WO93/15755 discloses a soluble thrombomodulin wherein the amino acid sequence is modified to prevent proteolysis by a proteolytic enzyme; and WO93/25675 discloses a soluble thrombomodulin wherein cofactor activity is modified by modifying the amino acid sequence. Doi et al. discloses a soluble thrombomodulin having added thereto an amino acid sequence containing an acidic amino acid sequence from bovine thrombomodulin (the Pharmaceutical Society of Japan, 113rd Meeting, Lecture Summaries 3, Lecture No. 30EM14-1, p128, 1993).

With regard to natural soluble thrombomodulins from human urine, Japanese Patent Application Laid-Open No. 63(1988)-30423 discloses a mixture of soluble thrombomodulins having molecular weights under non-reduced condition of 200,000, 48,000 and 40,000, respectively; Japanese Patent Application Laid-Open No. 63(1988)-146898 discloses soluble thrombomodulins having molecular weights under non-reduced condition of 39,000±10,000 and 31,000±10,000; Japanese Patent Application Laid-Open No. 3(1991)-86900 discloses soluble thrombomodulins having molecular weights under non-reduced condition of from 55,000 to 58,000 and from 60,000 to 65,000; and Japanese Patent Application Laid-Open No. 3(1991)-218399 discloses soluble thrombomodulins having molecular weights under non-reduced condition of 72,000±3,000 and 79,000±3,000. Ishii et al. discloses soluble thrombomodulins in plasma and urine (J. Clin. Invest., 76, 2178–2181, 1985); Hiramoto et al. discloses several soluble thrombomodulins in blood and urine (the Pharmaceutical Society of Japan, 108th Meeting, Lecture Summaries, Lecture No. 6F05 11-1, 1988); Yatani et al. discloses a soluble thrombomodulin having a molecular weight under reduced condition of 63,000 (Vessels (Ketsueki to Myakukan), 20, 197–200, 1989); and Yamamoto et al. discloses a soluble thrombomodulin comprising 468 amino acid residues (J. Biochem., 113, 433–440, 1993).

In spite of the advantageous high solubility, the soluble thrombomodulin is insufficient in its chemical stability. For example, even if the soluble thrombomodulin is lyophilized, it still suffers from diminished activity and formation of aggregates after prolonged storage at room temperature of several months to several years. Depending on the conditions of the lyophilization, the soluble thrombomodulin may also become slightly denatured. If the soluble thrombomodulin were denatured, and the denatured soluble thrombomodulin with the aggregates formed through such denaturing were administered to human blood, there would be a fair risk of the aggregates, which is a denatured protein, inducing hypersensitivity and other immunological responses as well as thrombosis. At present, even if the soluble thrombomodulin were to be used for a medicine, it is quite difficult to produce a preparation that can be reliably stored for a prolonged period of time without losing the quality required in the medical field.

Several reports are present that disclose particular types of sugars to be capable of stabilizing particular types of proteins. At the same time, some reports disclose that particular types of sugars are incapable of stabilizing particular types of proteins, or that particular types of sugars would destabilize particular types of proteins. For example, destabilization of tubulin by sucrose is disclosed in Biochem. Bhiophys. Acta., 532, 155–160, 1978; and Japanese Patent Application Laid-Open No. 59(1984)-59625 discloses that sugars such as glucose was capable of stabilizing the activity of tumor necrosis factor, while sugars such as lactose, maltose and sucrose were utterly incapable of stabilizing the activity of the tumor necrosis factor.

Production of preparations of thrombomodulin or thrombomodulin-like substances has scarcely been reported. In the "Detailed Description of the Invention" of Japanese Patent Application Laid-Open Nos. 1(1989)-6219 and 2(1990)-255699 and WO91/04276, there is an indication of the use in an injection of sucrose, glycerin, methylcellulose or carboxymethylcellulose as an additive for the purpose of increasing the viscosity of the injection. These references, however, are utterly silent about the stabilizing effect, and moreover, there is no illustrative demonstration for the stabilizing effect. Japanese Patent Application Laid-Open Nos. 1(1989)-6219, 2(1990)-255699 and 3(1991)-218399 and WO92/00325 describe formulations of the thrombomodulin wherein albumin, purified gelatin or mannitol is added. However, there is no description of the nature or the stability of the formulation not to mention the merit of the addition of such additives.

The inventors of the present invention have prepared a series of compositions containing the human urine soluble thrombomodulin together with albumin, purified gelatin, glycine, glucose, or mannitol, and evaluated the resulting compositions for their stability. However, such compositions failed to exhibit sufficient long term stability. As described above, no technique has been so far disclosed that would enable long term storage at room temperature of the soluble thrombomodulin preparation.

Specific activity of the soluble thrombomodulin is quite high. Accordingly, when the soluble thrombomodulin is clinically used, it is used at a quite minute dose, and it is often diluted to a very low concentration with an infusion for the purpose of continuous administration. It has been found that the soluble thrombomodulin that has been diluted to a low concentration with an infusion is likely to become adsorbed on the surface of the container such as a glass container, a plastic container, and an infusion bag and tubes, and in particular, on the plastic container and the infusion bag and tubes. This implies that there is a risk of decrease in the effective amount of the soluble thrombomodulin in actual administration. Known anti-adsorption means that have been reported include use of basic amino acid for preventing the adsorption of secretin (Japanese Patent Application Laid-Open No. 57(1982)-169425) and use of a cellulose derivative, a nonionic surface-active agent, or methylcyclodextrin for preventing the adsorption of the secretin, insulin and other low molecular weight peptides (Japanese Patent Application Laid-Open Nos. 58(1983)-206513, 59-76024, and 60(1985)-100524). No technique, however, has so far been disclosed for the prevention of the adsorption of the soluble thrombomodulin.

SUMMARY OF THE INVENTION

An object of the present invention is to provide a highly stable soluble thrombomodulin-containing composition which can be stored for a prolonged period. Another object of the present invention is to provide a highly stable soluble thrombomodulin-containing composition which would not exhibit adsorption of the soluble thrombomodulin onto the surface of the container after diluting to a lower concentration. More illustratively, the object of the present invention is to provide a lyophilized soluble thrombomodulin-containing composition that can be used as a highly safe, stable medicament even after storing for a prolonged period at room temperature. Furthermore, the object of the present invention is to provide a lyophilized soluble thrombomodulin-containing composition that can be used as a medicament that would not undergo decrease in the amount of the soluble thrombomodulin by the adsorption of the soluble thrombomodulin onto the container after diluting into an aqueous solution of a low concentration.

A further object of the present invention is to provide a stabilizing agent and a method for stabilizing the soluble thrombomodulin.

A still further object of the present invention is to provide an anti-adsorption agent and a method for preventing adsorption of the soluble thrombomodulin.

In order to solve the problems associated with the insufficient stability of the soluble thrombomodulin, the inventors of the present invention have made an intensive study of the soluble thrombomodulin, and in particular, in the lyophilized soluble thrombomodulin composition, and found that admixing of maltose (which may be α- or β-maltose or a mixture thereof at any desired mixing ratio; unless otherwise noted, the term, maltose includes all of these species), lactose (which may be α- or β-lactose or a mixture thereof at any desired mixing ratio; unless otherwise noted, the term, lactose includes all of these species), sucrose, or arginine (which may be D- or L-arginine or a racemic form thereof; unless otherwise noted, the term, arginine includes all of these species), or a salt thereof with the soluble thrombomodulin is highly effective in stabilizing the soluble thrombomodulin, and particularly, in stabilizing the soluble thrombomodulin for a prolonged period of time. It has also been found that a nonionic surface-active agent is effective in preventing the adsorption of the soluble thrombomodulin onto the surface of the container after its dilution to a low concentration. The present invention has been completed on such findings.

In view of the above findings, there is provided in accordance with the present invention a soluble thrombomodulin-containing composition comprising a soluble thrombomodulin and at least one member selected from maltose, lactose, sucrose, and arginine and a salt thereof as critical components; a thrombomodulin-containing composition further comprising a nonionic surface-active agent; and thrombomodulin-containing composition comprising a soluble thrombomodulin and a nonionic surface-active agent as critical components.

The soluble thrombomodulin may preferably be a human urine soluble thrombomodulin. It is also preferable to use a recombinant human soluble thrombomodulin for the soluble thrombomodulin. Accordingly, the soluble thrombomodulins that may be used in the present invention include those described in the known references cited in the foregoing "Background Art", which are incorporated herein by reference.

The human urine soluble thrombomodulin may preferably have a partial structure and properties as described below:
a) molecular weight: 72,000±3,000
(measured by sodium dodecyl sulfate (SDS)-polyacrylamide gel electrophoresis (PAGE) under non-reduced condition);
b) isoelectric point: 3.9±0.2;
c) terminal amino acid sequence
N terminal: Ala-Pro-Ala-Glu-Pro-Gln-Pro-Gly-Gly-Ser-Gln-Cys-Val-Glu-His-Asp-Cys-Phe-Ala-Leu-Tyr-Pro-Gly-Pro-Ala-Thr-Phe-Leu-( SEQ ID NO:1), and
C terminal: -Leu-Ala-Arg or -Leu-Val-Arg; and
d) sugar composition (% by weight):
neutral sugar: 5.5±1.0%
(measured by phenol sulphuric acid method),
amino sugar 2.2±1.0%
(measured by Elson-Morgan's method (Blix's modification)), and
sialic acid: 2.8±1.5%
(measured by Warren's method).

Alternatively, the human urine soluble thrombomodulin may preferably have a partial structure and properties as described below:
a) molecular weight: 79,000±3,000
(measured by SDS-PAGE under non-reduced condition);
b) isoelectric point: 3.8±0.2;
c) terminal amino acid sequence
N terminal: Ala-Pro-Ala-Glu-Pro-Gln-Pro-Gly-Gly-Ser-Gln-Cys-Val-Glu-His-Asp-Cys-Phe-Ala-Leu-Tyr-Pro-Gly-Pro-Ala-Thr-Phe-Leu-( SEQ ID NO:1), and
C terminal: -Leu-Ala-Arg or -Leu-Val-Arg; and
d) sugar composition (% by weight):
neutral sugar: 6.2±1.0%
(measured by phenol sulphuric acid method),
amino sugar 3.1±1.0%
(measured by Elson-Morgan's method (Blix's modification)), and
sialic acid: 3.8±1.5%
(measured by Warren's method).

According to the present invention, there is also provided a soluble thrombomodulin-containing composition comprising two or more molecular species of soluble thrombomodulins and at least one member selected from maltose, lactose, sucrose, and arginine and a salt thereof as critical components; a thrombomodulin-containing composition further comprising a nonionic surface-active agent; and a thrombomodulin-containing composition comprising soluble thrombomodulins and a nonionic surface-active agent as critical components. The preferable species of the soluble thrombomodulins used for the composition are the same as those used for the composition of the above-described aspect of the present invention.

The soluble thrombomodulin-containing composition according to the above-described aspects of the present invention may preferably be in the form of a lyophilized composition.

According to the present invention, there is also provided a use of the composition wherein the soluble thrombomodulin-containing composition comprising a soluble thrombomodulins and at least one member selected from maltose, lactose, sucrose, and arginine and a salt thereof as critical components; and a nonionic surface-active agent are separately prepared, and mixed immediately before the administration of the composition. The preferable species of the soluble thrombomodulins used for the composition are the same as those used for the composition of the above-described aspect of the present invention.

According to the present invention, there is also provided a method for producing a soluble thrombomodulin-containing composition comprising the step of preparing a solution of a soluble thrombomodulin and at least one member selected from the group consisting of maltose, lactose, sucrose, arginine and a salt thereof, and a nonionic surface-active agent.

According to the present invention, there is also provided a method for producing a soluble thrombomodulin-containing composition comprising the steps of preparing a solution of a soluble thrombomodulin and at least one member selected from the group consisting of maltose, lactose, sucrose, arginine and a salt thereof, and a nonionic surface-active agent; and lyophilizing the soluble thrombomodulin-containing composition in the form of the solution.

According to the present invention, there is also provided a method for producing a soluble thrombomodulin-containing composition comprising the step of preparing a solution of two or more molecular species of soluble thrombomodulins and at least one member selected from the group consisting of maltose, lactose, sucrose, arginine and a salt thereof, and a nonionic surface-active agent.

According to the present invention, there is also provided a method for producing a soluble thrombomodulin-containing composition comprising the steps of preparing a solution of two or more molecular species of soluble thrombomodulins and at least one member selected from the group consisting of maltose, lactose, sucrose, arginine and a salt thereof, and a nonionic surface-active agent; and lyophilizing the soluble thrombomodulin-containing composition in the form of the solution.

According to the present invention, there is also provided a method for stabilizing a soluble thrombomodulin comprising the step of adding at least one member selected from maltose, lactose, sucrose, and arginine and a salt thereof to the soluble thrombomodulin. According to the present invention, there is also provided a stabilizing agent for a soluble thrombomodulin comprising at least one member selected from maltose, lactose, sucrose, and arginine and a salt thereof. According to the present invention, there is also provided a method for preventing adsorption of a soluble thrombomodulin comprising the step of adding a nonionic surface-active agent to the soluble thrombomodulin; and an anti-adsorption agent for a soluble thrombomodulin comprising a nonionic surface-active agent.

According to the present invention, there is also provided a method for stabilizing two or more molecular species of soluble thrombomodulins comprising the step of adding at least one member selected from maltose, lactose, sucrose, and arginine and a salt thereof to the two or more molecular species of soluble thrombomodulins; and a method for preventing adsorption of two or more molecular species of soluble thrombomodulins comprising the step of adding a nonionic surface-active agent to the two or more molecular species of soluble thrombomodulins.

According to the present invention, there is also provided a soluble thrombomodulin-containing pharmaceutical composition comprising a pharmaceutically effective amount of a soluble thrombomodulin and at least one member selected from maltose, lactose, sucrose, and arginine and a salt thereof as critical components; a soluble thrombomodulin-containing pharmaceutical composition as described above further comprising a pharmaceutically acceptable nonionic surfactant; and a soluble thrombomodulin-containing pharmaceutical composition comprising a pharmaceutically effective amount of a soluble thrombomodulin and a pharmaceutically acceptable nonionic surface-active agent. According to the present invention, there is also provided a prophylactic/therapeutic agent for blood coagulation disorder-related diseases that is highly stable even after storing for a prolonged period of time and wherein the soluble thrombomodulin is prevented from being adsorbed onto the surface of the container after its dilution to a low concentration. The preferable species of the soluble thrombomodulins used are the same as those used for the composition of the above-described aspect of the present invention.

BEST MODE FOR CARRYING OUT THE INVENTION

The present invention is hereinafter described in further detail.

The soluble thrombomodulin used in the present invention may be either a natural soluble thrombomodulin or a genetically engineered soluble thrombomodulin. The genetically engineered soluble thrombomodulin may also be a modified soluble thrombomodulin or a chimeric soluble thrombomodulin. Typical soluble thrombomodulins are those described in conjunction with the prior art. When the composition of the present invention is used for a medicament, use of a soluble thrombomodulin of human origin is preferred, and in particular, use of a soluble thrombomodulin of human urine origin is preferred.

Typical natural soluble thrombomodulins include those described in Japanese Patent Application Laid-Open No. 3(1991)-218399 having a molecular weight under non-reduced condition of 72,000±3,000 (hereinafter referred to as UTM1) and 79,000±3,000 (hereinafter referred to as UTM2). Typical genetically engineered soluble thrombomodulins include recombinant human urine soluble thrombomodulins described in WO92/00325, and soluble thrombomodulin described in Japanese Patent Application Laid-Open No. 1(1989)-6219 comprising 498 amino acid residues with the amino terminal amino acid sequence of Ala-Pro-Ala-. When the soluble thrombomodulin is used for a medicament, the soluble thrombomodulin should be purified to a pharmaceutically acceptable level.

In the composition of the present invention, the soluble thrombomodulin may be used either alone or in a combination of two or more molecular species of the soluble thrombomodulins mixed at any desired mixing ratio. Typical such combinations are combination of 2 types of human urine soluble thrombomodulins disclosed in Japanese Patent Application Laid-Open No. 3(1991)-218399, and combination of soluble thrombomodulins having different sugar chain structures as disclosed in WO91/04276.

The natural soluble thrombomodulin may be produced in accordance with the method described in Japanese Patent Application Laid-Open No. 3(1991)-218399 or 3(1991)-86900.

The recombinant soluble thrombomodulin may be produced in accordance with the method described WO92/00325, Japanese Patent Application Laid-Open No. 1(1989)-6219, or WO91/04276.

The stabilizing agent used in the present invention may be a disaccharide having reducibility, sucrose, or an amino acid. More illustratively, in the present invention, at least one member selected from maltose, lactose, sucrose, and arginine and a salt thereof is used as the stabilizing agent in stabilizing the soluble thrombomodulin. The salt of the arginine may be either a salt with an inorganic acid or with an organic acid so long as the salt is pharmaceutically acceptable. Exemplary preferable salts are hydrochloride, citrate, and sulfate, the hydrochloride being the most preferred. The amount of such stabilizing agent used is not limited to any particular range. Typical amount used is in the range of from about 0.1 mg to about 1,000 mg per 1 mg titer of the soluble thrombomodulin. The amount used may preferably be from about 0.5 mg to about 500 mg, and more preferably, from about 0.5 mg to about 100 mg per 1 mg titer of the soluble thrombomodulin. When the composition is to be lyophilized and the additive used for the stabilization of the soluble thrombomodulin is sucrose, use of a somewhat smaller amount is preferred since a lyophilized composition containing the sucrose at a high mixing ratio in relation to the soluble thrombomodulin may collapse during its storage. Preferred amount of the sucrose used is in the range of from about 0.5 mg to about 50 mg per 1 mg titer of the soluble thrombomodulin. If desired, a high molecular weight compound such as dextran may be used in combination with the sucrose in order to prevent such collapse.

It should be noted that the stabilizing agent selected from maltose, lactose, sucrose, and arginine and a salt thereof is preferably used at an amount of 100 mg or less per 1 ml of the solution (composition) containing the soluble thrombomodulin. In addition to the effect of stabilizing the soluble thrombomodulin, such stabilizing agent may additionally serve as a diluent, buffering agent, isotonizing agent, dispersing agent, or the like depending on the amount used. Therefore, the amount of such additive used should be determined by taking the intended use of the resulting composition into consideration.

The anti-adsorption agent used in the present invention is a surface-active agent which may preferably be a nonionic surface-active agent. The nonionic surface-active agent may preferably the one that is pharmaceutically acceptable, and it not limited to any particular species. Exemplary preferable surface-active agent include an ethylene oxide-propylene oxide copolymer, a poly(oxyalkylene) mono- or tri-sorbitan ester (a fatty acid ester of sorbitol and an anhydride thereof that has been copolymerized with various molar numbers of ethylene oxide), polyoxyethylene-hardened caster oil, and the like. Typical ethylene oxide-propylene oxide copolymers include Pluronic F68, Poloxamer 188, etc.; and typical poly(oxyalkylene) mono- or tri-sorbitan esters include Polysorbate 80 (olate ester), Polysorbate 20 (laurate ester), Polysorbate 40 (palmitate ester), Polysorbate 69 (stearate ester), etc.; and typical polyoxyethylene-hardened caster oils include HCO40, HCO60, etc. One or more nonionic surface-active agents selected from the above-mentioned species may be used in the present invention, and when one nonionic surface-active agent is used, it is preferable to use an ethylene oxide-propylene oxide copolymer or a poly(oxyalkylene) mono- or tri-sorbitan ester; and more preferably, Pluronic F68, Polysorbate 80, or Polysorbate 20; and most preferably, Pluronic F68.

The amount of the nonionic surface-active agent added as an anti-adsortpion agent is not limited to any particular range. When the soluble thrombomodulin-containing composition is in the form of an aqueous solution, the nonionic surface-active agent may be desirably used at a concentration of 0.00005% by weight or higher. In other words, the nonionic surface-active agent may be desirably used at a sufficiently low concentration at which the nonionic surface-active agent itself would not exhibit any pharmaceutical activity in the living body after its administration. In conjunction with such consideration, the nonionic surface-active agent may be desirably used in an aqueous solution of the soluble thrombomodulin of at a concentration of 1% by weight or less. The effectivity of the anti-adsorption component may vary in accordance with its concentration and with the material and surface area of the container, and therefore, the nonionic surface-active agent may be used at a suitable amount in accordance with the dilution ratio of the composition in clinical use, or material and size of the container used for the dilution. Preferably, use of the nonionic surface-active agent at an amount that would result in the above-described concentration of from 0.00005 to 1% by weight is suitable for attaining the objects of the present invention. In addition, it is preferable to use the nonionic surface-active agent at an amount that would reach a concentration of from 0.0001 to 0.01% by weight in the body when its administration.

The maltose, lactose, sucrose, and arginine and a salt thereof, or a nonionic surface-active agent used in the present invention as an essential component for stabilization or anti-adsorption may be used either alone or as a combination of two or more. Typical combinations include maltose and a nonionic surface-active agent; lactose and a nonionic surface-active agent; sucrose and a nonionic surface-active agent; arginine and a nonionic surface-active agent; maltose and arginine; lactose and arginine; sucrose and arginine; maltose and lactose; maltose and sucrose; lactose and sucrose; maltose, lactose, and sucrose; maltose, arginine and a nonionic surface-active agent; lactose, arginine and a nonionic surface-active agent; and sucrose, arginine and a nonionic surface-active agent; and mixing ratio of the components is not limited to any particular range. In the above-mentioned combinations, the nonionic surface-active agent may be used either alone or in combination of two or more.

Of the above-mentioned combinations, the preferred are combinations of at least one member selected from maltose, lactose, sucrose and arginine together with a nonionic surface-active agent, and preferred nonionic surface-active agents used in such combinations are Pluronic F68, Polysorbate 80 and Polysorbate 20, among which Pluronic F68 being the most preferred. In other words, the most preferable combinations are maltose and Pluronic F68; lactose and Pluronic F68; sucrose and Pluronic F68; and arginine and Pluronic F68, which may be mixed at any desired mixing ratio.

The soluble thrombomodulin-containing composition of the present invention may contain any desired stabilizers, preservatives, antiseptics, buffering agents, thickening agents, surface-active agents, or the like that is required for the intended use of the composition in addition to the soluble thrombomodulin and the at least one critical component selected from maltose, lactose, sucrose, and arginine and a salt thereof. Alternatively, the soluble thrombomodulin-containing composition of the present invention may contain any desired stabilizers, preservatives, antiseptics, buffering agents, thickening agents, surface-active agents, or the like that is required for the intended use of the composition in addition to the soluble thrombomodulin, the at least one critical component selected from maltose, lactose, sucrose, and arginine and a salt thereof, and the nonionic surface-active agent. The soluble thrombomodulin-containing composition of the present invention may contain any desired stabilizers, preservatives, antiseptics, buffering agents, thickening agents, surface-active agents, or the like that is required for the intended use of the composition in addition to the soluble thrombomodulin and the nonionic surface-active agent. The lyophilized preparation used for medication may contain any of preservatives, stabilizers, binders, diluents, disintegrants, moistening agents, lubricants, coloring agents, aromatic agents, flavoring agents, suspending agents, emulsifiers, solubilizers, buffering agents, isotonizing agents, surface-active agents, adsorption-preventing agents, soothing agents, and the like in accordance with the intended use of the preparation. In particular, inclusion in the preparation of a buffering agent for pH adjustment and a isotonizing agent for osmotic pressure adjustment is preferred. Although the type and the amount of the above-mentioned additives do not essentially influence the nature of the present invention, use of salf of such additive at an excessively high concentration is not preferable in view of the inhibition of the cake formation during lyophilization.

The soluble thrombomodulin-containing composition of the present invention may be produced by dissolving at least one member selected from maltose, lactose, sucrose, arginine and a salt thereof, and a nonionic surface-active agent in a solution containing the soluble thrombomodulin that has been prepared as described above to thereby produce a solution.

Alternatively, the soluble thrombomodulin-containing composition of the present invention may be produced by mixing the lyophilized soluble thrombomodulin with the at least one member selected from maltose, lactose, sucrose, arginine and a salt thereof, and a nonionic surface-active agent; and dissolving the mixture in a suitable solvent such as distilled water or physiological saline, or alternatively, in a suitable buffer solution. In either case, the resulting soluble thrombomodulin-containing composition comprises the soluble thrombomodulin and the at least one member selected from maltose, lactose, sucrose, arginine a salt thereof, and a nonionic surface-active agent dissolved in a solution. It should also be noted that, in either case, the at least one member selected from maltose, lactose, sucrose, arginine and a salt thereof, and a nonionic surface-active agent may be dissolved in a suitable solvent before mixing with the soluble thrombomodulin. When the soluble thrombomodulin-containing composition is used as a medicament, the additives used should be of pharmaceutically acceptable grade.

The thus prepared solution may be lyophilized by a conventional procedure to prepare the composition in cake or powder form. When the soluble thrombomodulin-containing composition is used as a medicament, the solution may preferably be aseptically filtered and filled in vials, ampoules, or the like, and if desired, the thus filled solution may be lyophilized by a conventional procedure to produce a lyophilized preparation.

When the soluble thrombomodulin-containing composition is used as a medicament, it may be administered by a conventional administration procedure, namely, parenteral administration such as intravenous, intramuscular, or subcutaneous administration. The thrombomodulin-containing composition in the form of lyophilized preparation may be dissolved in water for injection before its use, and then administered to the patient. Oral administration is not effective since the administered medicament would be subject to decomposition in digestive tract. However, the composition can be orally administered if the composition is incorporated in liposomes, microspheres, nanospheres or the like that are less likely to be decomposed in the digestive tract. The composition can also be administered permucosally from mucous membrane in rectum, nasal cavity, or hypoglottis.

Typical daily dose is 0.005 to 500 mg titer, and preferable daily dose is 0.1 to 10 mg titer as disclosed in Japanese Patent Application Laid-Open No. 3(1991)-218399. The dose, however, may be suitably adjusted by taking the age, weight, conditions and the like of the patient into consideration.

The thus produced composition of the present invention is stable throughout the processes of freezing, drying, storage, temperature elevation, and dissolution, and has an excellent long term storability at room temperature. The stabilizing agent and the anti-adsorption agent that have been found effective for use in the soluble thrombomodulin composition of the present invention are highly safe, and when the composition of the present invention is used for a medicament, such additives enable the high quality of the medicament to be retained for a prolonged period with no risk of inactivation or aggregate formation. In addition, when the composition of the present invention is diluted to constitute an aqueous solution of low concentration, the soluble thrombomodulin is prevented from being adsorbed onto the container surface, and therefore, the composition of the present invention would not undergo a decrease in the effective amount of the soluble thrombomodulin even when it is diluted with an infusion at clinical sites. Therefore, the soluble thrombomodulin-containing composition of the present invention would constitute a highly safe, room temperature-storable prophylactic or therapeutic agent that can be used for blood coagulation disorder-related diseases. The soluble thrombomodulin-containing composition of the present invention would also constitute a prophylactic or therapeutic agent that can be used for blood coagulation disorder-related diseases wherein the adsorption of the effective component onto the container surface is prevented. The composition, the production method, the stabilization agent, the stabilization method, the anti-adsorption agent, and the anti-adsorption method of the present invention may also be utilized in the purification of the soluble thrombomodulin, or in the storage of soluble thrombomodulin stock.

EXAMPLES

The present invention is hereinafter described in further detail by referring to the Examples.

Preparation of soluble thrombomodulin-1
Purification of human urine soluble thrombomodulin Human urine soluble thrombomodulin was prepared in accordance with the procedure described in Japanese Patent Application Laid-Open No. 3(1991)-218399. 100 liters of stock urine was adjusted to pH 8.5 with 10% NaOH and the precipitate was removed. The urine was then adjusted to pH 5.5 with 4M HCl, and filtered through acrylonitrile fiber to adsorb and remove urokinase in the urine. The filtrate urine was desalted and concentrated by ultrafiltration through a ultrafiltration membrane of 40,000-molecular weight cutoff.

The urine concentrate was adjusted to pH 7.3, and heated to 60° C. for 15 minutes. The urine was then passed through a 300 ml column of DEAE-cellulose (manufactured by Whatman) that had been conditioned with 0.05M phosphate buffered saline, pH 6.5 containing 0.068M NaCl for adsorption of the active fraction in the urine. The column was washed with 750 ml of the buffer which was the same as the one used for the conditioning of the column, and subsequently, the adsorbed active fraction was eluted from the column with acetate buffer, pH 4.0 containing 0.05M NaCl.

The eluate was concentrated with a ultrafiltration membrane of 30,000-molecular weight cutoff, and adjusted to pH 7.5 with 2M NaOH, and passed through a 2.5 ml column of DIP-thrombin-agarose that had been conditioned with 0.02M Tris-HCl buffer, pH 7.5 containing 0.1M NaCl, 1 mM benzamidine hydrochloride, and 0.5 mM $CaCl_2$ for adsorption of the active fraction.

The column was then washed with 25 ml of the buffer which was the same as the one used for the conditioning of the column, and the adsorbed active fraction was eluted from the column with 0.02M Tris-HCl buffer, pH 7.5 containing 1M NaCl, 1 mM benzamidine hydrochloride, and 0.5 mM EDTA. The eluate was then dialyzed against the buffer which was the same as the one used for the conditioning of the column, and purified by DIP-thrombin-agarose chromatography on a column which had a volume the same as the one used in the previous DIP-thrombin-agarose chromatography and which had been similarly conditioned. The same column was used for the second DIP-thrombin-agarose chromatography, and the column was washed with 10 ml of the buffer which was the same as the one used for the conditioning of the column, and then, with 10 ml of 0.02M Tris-HCl buffer, pH 7.5 containing 0.8M NaCl, 1 mM benzamidine hydrochloride, and 0.5 mM $CaCl_2$. The adsorbed active fraction was eluted from the column with 0.02M Tris-HCl buffer, pH 7.5 containing 1M NaCl, 1 mM benzamidine hydrochloride, and 0.5 mM EDTA.

The eluate was concentrated with a ultrafiltration membrane of 30,000-molecular weight cutoff, and the concentrate was subjected to gel filtration on 500 ml column of Sephacryl S-300 (manufactured by Pharmacia Fine Chemicals) that had been conditioned with 0.01M phosphate buffered saline, pH 7.0 containing 0.14M NaCl to collect the active fraction (UTM0). In other series of purification, an active fraction (UTM1) corresponding to a molecular weight of 72,000±3,000, and an active fraction (UTM2) corresponding to a molecular weight of 79,000±3,000 as measured by SDS-PAGE under non-reduced condition were collected. The thus obtained fractions were dialyzed against distilled water overnight, and lyophilized.

The resulting natural human urine soluble thrombomodulins, i.e. UTM1 and UTM2 had the partial structure and the properties as described below.

(1) UTM1
  a) molecular weight: 72,000±3,000
    (measured by sodium dodecyl sulfate (SDS)-polyacrylamide gel electrophoresis (PAGE) under non-reduced condition);
  b) isoelectric point: 3.9±0.2;
  c) terminal amino acid sequence
    N terminal: Ala-Pro-Ala-Glu-Pro-Gln-Pro-Gly-Gly-Ser-Gln-Cys-Val-Glu-His-Asp-Cys-Phe-Ala-Leu-Tyr-Pro-Gly-Pro-Ala-Thr-Phe-Leu-( SEQ ID NO:1), and
    C terminal: -Leu-Ala-Arg or -Leu-Val-Arg; and
  d) sugar composition (% by weight):
    neutral sugar: 5.5±1.0%
      (measured by phenol sulphuric acid method),
    amino sugar 2.2±1.0%
      (measured by Elson-Morgan's method (Blix's modification)), and
    sialic acid: 2.8±1.5%
      (measured by Warren's method).

(2) UTM2
  a) molecular weight: 79,000±3,000
    (measured by SDS-PAGE under non-reduced condition);
  b) isoelectric point: 3.8±0.2;
  c) terminal amino acid sequence
    N terminal: Ala-Pro-Ala-Glu-Pro-Gln-Pro-Gly-Gly-Ser-Gln-Cys-Val-Glu-His-Asp-Cys-Phe-Ala-Leu-Tyr-Pro-Gly-Pro-Ala-Thr-Phe-Leu-( SEQ ID NO:1), and
    C terminal: -Leu-Ala-Arg or -Leu-Val-Arg; and
  d) sugar composition (% by weight):
    neutral sugar: 6.2±1.0%
      (measured by phenol sulphuric acid method),
    amino sugar 3.1±1.0%
      (measured by Elson-Morgan's method (Blix's modification)), and
    sialic acid: 3.8±1.5%
      (measured by Warren's method).

Preparation of soluble thrombomodulin-2
Preparation of genetically engineered recombinant human soluble thrombomodulin (RTM1)

Recombinant human soluble thrombomodulin was prepared in accordance with the method described in WO92/00325. A vector expressing soluble thrombomodulin (ruTM-Ala) comprising 456 amino acid residues was prepared by utilizing a DNA probed from human placental cDNA library, and the resulting vector was introduced in CHO cell. Gene amplification was conducted to produce a cell line of high expression. The culture medium of the high expression cell line was purified by DIP-thrombin-agarose column chromatography and gel filtration to obtain the desired product (RTM1).

Preparation of soluble thrombomodulin-3
Preparation of genetically engineered recombinant human soluble thrombomodulin (RTM2)

Recombinant human soluble thrombomodulin was prepared in accordance with the method described in WO92/00325. A vector expressing soluble thrombomodulin comprising 498 amino acid residues having amino terminal amino acid sequence of Ala-Pro-Ala- was prepared by utilizing a DNA probed from human placental cDNA library, and the resulting vector was introduced in CHO cell. Gene amplification was conducted to produce a cell line of high expression. The culture medium of the high expression cell line was purified by DIP-thrombin-agarose column chromatography and gel filtration to obtain the desired product (RTM2).

The present invention is further described by referring to the following experiments, which by no means limit the scope of the invention.

Experiment 1

UTM0 prepared in the above-described "Preparation of soluble thrombomodulin-1" was used to prepare the lyophilized injections as shown below. The injections were stored in an incubator at 50° C., and evaluated for their residual titer after storing for 3 and 6 months, and for their aggregation formation rate after storing for 6 months by the procedure as described below. The results are shown in Tables 1 and 2. It should be noted that the percentage of the residual titer shown in Table 1 is the percentage of the residual titer after storing at 50° C. in relation to the residual titer of the same injection after storing at 4° C. for the same period. The UTM0 used in the experiment contained 69% of the UTM1 and 31% of the UTM2.

Preparation 1
In 30 ml of distilled water adapted for use in preparing injections were dissolved 75 mg titer of UTM0 and 300 mg of maltose. The resulting solution was aseptically filtered, and the filtrate was filled in sterilized glass vials in 1 ml portions. The content of the vials was then lyophilized to prepare the injection that is to be dissolved before its use.

The above-described procedure was repeated by using the ingredients as described below to prepare Preparations 2 to 9.

| Preparation 2 | |
|---|---|
| UTM0 | 75 mg titer |
| Lactose | 300 mg |
| Preparation 3 | |
| UTM0 | 75 mg titer |
| Sucrose | 300 mg |
| Preparation 4 | |
| UTM0 | 75 mg titer |
| Arginine hydrochloride | 600 mg |
| Preparation 5 | |
| UTM0 | 75 mg titer |
| Glucose | 300 mg |
| Preparation 6 | |
| UTM0 | 75 mg titer |
| Mannitol | 300 mg |
| Preparation 7 | |
| UTM0 | 75 mg titer |
| Glycine | 600 mg |
| Preparation 8 | |
| UTM0 | 75 mg titer |
| Purified gelatin | 600 mg |
| Preparation 9 | |
| UTM0 | 75 mg titer |
| Human serum albumin | 300 mg |

Measurement of titer

The preparations were evaluated for their ability to activate protein C in the presence of thrombin by using Glu-Pro-Arg-p-NA (manufactured by Kabi) for the synthetic substrate. Human urine soluble thrombomodulin (UTM0) purified by Mochida Pharmaceutical Co., Ltd. was used for the standard.

The standard soluble thrombomodulin and the soluble thrombomodulin-containing preparations were respectively diluted with 0.05% Tween 20/Tris-HCl buffer, pH 8.4 to a suitable concentration. To 20 μl of the dilution was added 60 μl of 20 mM CaCl$_2$/Tris-HCl buffer, pH 8.4, and then 20 μl of bovine thrombin (manufactured by Mochida Pharmaceutical Co., Ltd.), and the reaction was promoted at room temperature for 20 minutes. To the reaction mixture was added 20 μl of 12 U/ml solution of human protein C (manufactured by American Diagnostica), and the reaction was promoted at room temperature for 20 minutes. To the reaction solution was added 80 μl of mixed solution of human antithrombin III (manufactured by The Green Cross Corporation) and heparin (manufactured by Mochida Pharmaceutical Co., Ltd.) to a final concentrations of 0.15 U/ml and 15 U/ml, respectively, and the reaction was promoted at room temperature for 20 minutes. 125 μl of the reaction solution was aliquoted, and 125 μl of 3 mM solution of the synthetic substrate was added to the aliquoted reaction solution. Absorption at a wave length of 405 nm was continuously measured at room temperature to determine initial reaction rate. A calibration curve was depicted by using the standard solution, and the titer of the preparations was evaluated by referring to the calibration curve. The thus determined titer was converted to the titer of rabbit lung thrombomodulin according to the description of Japanese Patent Application Laid-Open No. 3(1991)-218399.

Measurement of aggregation formation rate

Aggregation formation rate of the soluble thrombomodulin was measured by gel filtration using TSK-gel™ G3000 SW$_{XL}$ (manufactured by Toyo Soda Mfg. Co., Ltd.).

TABLE 1

| | Additive | | Residual titer (%) | |
|---|---|---|---|---|
| | Type | Amt. (mg) | 3 months | 6 months |
| Examples | | | | |
| Preparation 1 | maltose | 300 | 99.6 | 98.9 |
| Preparation 2 | lactose | 300 | 99.8 | 99.3 |
| Preparation 3 | sucrose | 300 | 98.4 | 98.7 |
| Preparation 4 | arginine hydrochloride | 600 | 99.6 | 99.6 |
| Comparative Examples | | | | |
| Preparation 5 | glucose | 300 | 96.0 | 97.6 |
| Preparation 6 | mannitol | 300 | 91.3 | 89.3 |
| Preparation 7 | glycine | 600 | 92.9 | 82.2 |
| Preparation 8 | purified gelatin | 600 | 89.0 | 95.6 |
| Preparation 9 | HSA | 300 | 87.7 | 84.8 |

TABLE 2

| | Additive | | Aggregation formation rate (%) | |
|---|---|---|---|---|
| | Type | Amt. (mg) | Immediately after lyphilization | After 6 months |
| Examples | | | | |
| Preparation 1 | maltose | 300 | 0.0 | 0.8 |
| Preparation 2 | lactose | 300 | — | 0.0 |
| Preparation 3 | sucrose | 300 | — | 0.6 |
| Preparation 4 | arginine hydrochloride | 600 | 0.0 | 0.0 |
| Comparative Examples | | | | |
| Preparation 5 | glucose | 300 | 1.4 | 3.4 |
| Preparation 6 | mannitol | 300 | 0.0 | 4.0 |
| Preparation 7 | glycine | 600 | — | 5.7 |

As shown in Tables 1 and 2, the stabilization effect of the additive on the human urine soluble thrombomodulin was significant in the case of maltose, lactose, sucrose, and arginine hydrochloride compared to the case of other common additives such as glucose, mannitol, glycine, purified gelatin, and human serum albumin (HSA). In other words, the human soluble thrombomodulin underwent a significant increase in its storage stability. The stabilization effect was most significant when lactose and arginine hydrochloride were added.

Experiment 2

UTM1 and UTM2 prepared in the above-described "Preparation of soluble thrombomodulin-1" were used to prepare the lyophilized compositions as shown below. The compositions were stored in an incubator at a temperature of 40° C. and at a humidity of 75%. After storing for 6 months, the compositions were evaluated for their residual titer and aggregation formation rate by repeating the procedure of Experiment 1. The results are shown in Tables 3 and 4. The percentage of the residual titer shown in Table 3 is the percentage of the titer after the storage in relation to the titer before the storage.

Composition 1

In 1 ml of purified water were dissolved 2.5 mg titer of UTM2 and 10 mg of maltose, and the resulting solution was lyophilized.

The above-described procedure was repeated to prepare the Compositions 2 to 8 by using the ingredients as described below.

Composition 2

| UTM1    | 2.5 mg titer |
| Lactose | 10 mg        |

Composition 3

| UTM2                  | 2.5 mg titer |
| Arginine hydrochloride | 20 mg       |

Composition 4

| UTM1    | 2.5 mg titer |
| Sucrose | 10 mg        |

Composition 5

| UTM1     | 2.5 mg titer |
| Mannitol | 10 mg        |

Composition 6

| UTM1    | 2.5 mg titer |
| Glycine | 20 mg        |

Composition 7

| UTM1             | 2.5 mg titer |
| Purified gelatin | 20 mg        |

Composition 8

| UTM1 | 2.5 mg titer |
| HSA  | 10 mg        |

TABLE 3

|  | Soluble thrombomodulin | | Additive | | Residual titer (%) | |
| --- | --- | --- | --- | --- | --- | --- |
|  | Type | mg titer | Type | Amt. (mg) | Immediately after lyophilization | After 6 months |
| Examples |  |  |  |  |  |  |
| Composition 1 | UTM2 | 2.5 | maltose | 10 | 100.2 | 99.1 |
| Composition 2 | UTM1 | 2.5 | lactose | 10 | — | 102.3 |
| Composition 3 | UTM2 | 2.5 | arginine hydrochloride | 20 | — | 100.9 |
| Composition 4 | UTM1 | 2.5 | sucrose | 10 | — | 99.6 |
| Comparative Examples |  |  |  |  |  |  |
| Composition 5 | UTM1 | 2.5 | mannitol | 10 | 99.8 | 96.5 |
| Composition 6 | UTM1 | 2.5 | glycine | 20 | — | 96.2 |
| Composition 7 | UTM1 | 2.5 | purified gelatin | 20 | 102.3 | 87.3 |
| Composition 8 | UTM1 | 2.5 | HSA | 10 | — | 90.9 |

TABLE 4

|  | Soluble thrombomodulin | | Additive | | Aggregation formation rate (%) |
| --- | --- | --- | --- | --- | --- |
|  | Type | mg titer | Type | Amt. (mg) |  |
| Examples |  |  |  |  |  |
| Composition 1 | UTM2 | 2.5 | maltose | 10 | 0.7 |
| Composition 2 | UTM1 | 2.5 | lactose | 10 | 0.4 |
| Composition 3 | UTM2 | 2.5 | arginine hydrochloride | 20 | 0.0 |
| Composition 4 | UTM1 | 2.5 | sucrose | 10 | 0.0 |

TABLE 4-continued

|  | Soluble thrombomodulin | | Additive | | Aggregation |
|---|---|---|---|---|---|
|  | Type | mg titer | Type | Amt. (mg) | formation rate (%) |
| Comparative Examples | | | | | |
| Composition 5 | UTM1 | 2.5 | mannitol | 10 | 4.0 |
| Composition 6 | UTM1 | 2.5 | glycine | 20 | 2.9 |

As shown in Tables 3 and 4, the stabilization effect of the additive on the human urine soluble thrombomodulin was significant in the case of maltose, lactose, sugar, and arginine hydrochloride compared to the case of other common additives, and the stabilization effect in the case of long term storage was particularly significant.

Experiment 3
Evaluation of the stability of the solution

UTM0 prepared in the above-described "Preparation of soluble thrombomodulin-1" was used to prepare 0.05 mg titer/ml soluble thrombomodulin solution containing 0.5 to 5 mg/ml maltose, lactose, sucrose or arginine hydrochloride. The resulting solution was stored at room temperature for 24 hours, and the residual titer was measured after the storage by the procedure described in Experiment 1. No solution exhibited significant loss of the activity.

If the soluble thrombomodulin became denatured to form aggregates, and the composition including such aggregates were introduced into human blood, there is a risk that the aggregates comprising a denatured protein may induce immunological response such as hypersensitivity or thrombosis. Accordingly, low aggregation formation rate is a merit of great importance for a medical preparation used for injection. In developing preparations, storability at room temperature of the preparation is generally determined by evaluating the stability of the preparation after storing 6 month at 40° C. The soluble thrombomodulin-containing preparation of the present invention was quite stable after storing for 6 month under more severe conditions of 50° C. as demonstrated in the experiments as described above. The soluble thrombomodulin-containing composition in the form of a solution also had a good storability. Therefore, when the soluble thrombomodulin-containing composition in the form a lyophilized preparation is dissolved before use, the solution can be safely used.

Experiment 4

UTM0 prepared in the above-described "Preparation of soluble thrombomodulin-1" was used to prepare the compositions in the form of solution as described below to evaluate the titer. In addition to such solutions, a contrast solution was prepared by dissolving 2.5 mg titer of UTM0 by 2.0 ml of physiological saline, and the contrast solution was also evaluated for its titer. To physiological saline (100 ml) in a plastic container was added 0.24 ml of the thus prepared solution using a syringe to dilute the soluble thrombomodulin to a theoretical final concentration of about 0.003 mg titer/ml. The thus diluted solution was collected 3 hours after the dilution to evaluate the residual titer. The titer was evaluated by repeating the procedure of Experiment 1, above.

Composition 9

2.5 mg titer of UTM0 was mixed with 5 mg of Polysorbate 80, and the mixture was dissolved in 2 ml of physiological saline.

Composition 10

2.5 mg titer of UTM0 was mixed with 10 mg of purified gelatin, and the mixture was dissolved in 2 ml of physiological saline.

TABLE 5

|  | Additive | | Residual titer (%) after storage |
|---|---|---|---|
|  | Type | Final conc. (%) | in a container (Plastic bottle) |
| Example | | | |
| Composition 9 | Polysorbate 80 | 0.0006 | 96.9 |
| Comparative Example | | | |
| Composition 10 | purified gelatin | 0.0012 | 87.5 |
| Contrast | | | |
|  | — | — | 79.6 |

As shown in Table 5, human urine soluble thrombomodulin exhibited a marked adsorption onto the plastic container. Anti-adsorption effect attained by the addition of Polysorbate 80 was more significant than the effect attained by the addition of the pure gelatin.

Experiment 5

UTM0 prepared in the above-described "Preparation of soluble thrombomodulin-1" was used to prepare the compositions in the form of solution as described below to evaluate the titer. In addition to such solutions, a contrast solution was prepared by dissolving 2.5 mg titer of UTM0 by 2.0 ml of physiological saline, and the contrast solution was also evaluated for its titer. An infusion system (TERU fusion® TS-A200CK, manufacture by TERUMO) was mounted to a plastic container filled with physiological saline, and 1 ml of the thus prepared solution was added to the physiological saline (500 ml, OTSUKA SEISHOKU CHU manufactured by Otsuka Pharmaceuticals Co., Ltd. in the plastic container) to dilute the soluble thrombomodulin to a theoretical final concentration of about 0.0025 mg titer/ml. The solution that had passed through the infusion set immediately after the dilution and the solution that was directly collected from the plastic bottle were evaluated for their residual titer. The titer was evaluated by repeating the procedure of Experiment 1, above.

Composition 11

2.5 mg titer of UTM0 was mixed with 1 mg of Polysorbate 80, and the mixture was dissolved in 2 ml of physiological saline.

The above-described procedure was repeated to prepare the Compositions 2 to 6 by using the ingredients as described below.

| Composition 12 | |
|---|---|
| UTM0 | 2.5 mg titer |
| Polysorbate 80 | 0.5 mg |
| Composition 13 | |
| UTM0 | 2.5 mg titer |
| Polysorbate 20 | 1 mg |
| Composition 14 | |
| UTM0 | 2.5 mg titer |
| Polysorbate 20 | 0.5 mg |
| Composition 15 | |
| UTM0 | 2.5 mg titer |
| Pluronic F68 | 5 mg |
| Composition 16 | |
| UTM0 | 2.5 mg titer |
| Pluronic F68 | 1 mg |

| Preparation 11 | |
|---|---|
| UTM0 | 150 mg titer |
| Arginine hydrochloride | 1200 mg |
| Polysorbate 80 | 69 mg |
| Purified gelatin | 300 mg |
| Preparation 12 | |
| UTM0 | 150 mg titer |
| Maltose | 600 mg |
| Pluronic F68 | 60 mg |
| Preparation 13 | |
| UTM0 | 150 mg titer |
| Maltose | 600 mg |
| Pluronic F68 | 60 mg |
| Purified gelatin | 300 mg |

TABLE 6

| | Additive | | Residual titer (%) after passing | Residual titer (%) after storage |
|---|---|---|---|---|
| | Type | Final conc. (%) | through the infusion system | in a container (Plastic bottle) |
| Example | | | | |
| Composition 11 | Polysorbate 80 | 0.0001 | 87.4 | 103.3 |
| Composition 12 | Polysorbate 80 | 0.00005 | 86.2 | 87.0 |
| Composition 13 | Polysorbate 20 | 0.0001 | 84.2 | 91.3 |
| Composition 14 | Polysorbate 20 | 0.00005 | 83.6 | 83.4 |
| Composition 15 | Pluronic F68 | 0.0005 | 94.8 | 92.2 |
| Composition 16 | Pluronic F68 | 0.0001 | 92.7 | 87.5 |
| Contrast | — | — | 63.3 | 79.1 |

As shown in Table 6, addition of Polysorbate 80, Polysorbate 20 and Pluronic F68 at a concentration of 0.00005% by weight or higher was effective in retaining the activity of the diluted solution of the human urine soluble thrombomodulin both in the infusion set and in the plastic container.

Experiment 6

UTM0 prepared in the above-described "Preparation of soluble thrombomodulin-1" was used to prepare the lyophilized injections as shown below. The injections were stored in an incubator at 50° C., and evaluated for their residual titer after storing for 3 and 6 months. The titer was evaluated by repeating the procedure of Experiment 1, above. The results are shown in Table 7. It should be noted that the residual titer is shown in terms of percentage in relation to the titer immediately after the lyophilization.

Preparation 10

In 60 ml of distilled water adapted for use in preparing injections were dissolved 150 mg titer of UTM0, 1200 mg of arginine hydrochloride, and 60 mg of Pluronic F68. The resulting solution was aseptically filtered, and the filtrate was filled in sterilized glass vials in 2 ml portions. The content of the vials was then lyophilized to prepare the injection that is to be dissolved before its use.

The above-described procedure was repeated by using the ingredients as described below to prepare Preparations 11 to 13.

TABLE 7

| | Additive | | Residual titer (%) | |
|---|---|---|---|---|
| | Type | Amt. (mg) | 3 months | 6 months |
| Examples | | | | |
| Preparation 10 | arginine hydrochloride | 1200 | 100.4 | 101.0 |
| | Pluronic F68 | 60 | | |
| Preparation 11 | arginine hydrdchloride | 1200 | 99.3 | 100.2 |
| | Polysorbate 80 | 60 | | |
| | purified gelatin | 300 | | |
| Preparation 12 | maltose | 600 | 100.4 | 100.1 |
| | Pluronic F68 | 60 | | |
| Preparation 13 | maltose | 600 | 99.2 | 99.7 |
| | Pluronic F68 | 60 | | |
| | purified gelatin | 300 | | |

As shown in Table 7, addition of arginine or maltose in combination with a nonionic surface-active agent resulted in a significant improvement in long-term storability of the human urine soluble thrombomodulin. The results confirmed the availability of a soluble thrombomodulin-containing composition having an excellent stability to endure long-term storage which would not exhibit adsorption of the soluble thrombomodulin on the container surface after dilution to a low concentration.

EXAMPLES OF PREPARATIONS

The present invention is further illustrated by referring the following examples, which by no means limit the scope of the invention.

Example 1

| | |
|---|---|
| UTM0 | 10 mg titer |
| Lactose | 100 mg |
| Purified gelatin | 100 mg |

The ingredients were dissolved in distilled water adapted for use in preparing injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 2

| | |
|---|---|
| UTM0 | 25 mg titer |
| Lactose | 100 mg |
| Pluronic F68 | 10 mg |
| Disodium hydrogenphosphate dodecahydrate | 0.77 mg |
| Sodium dihydrogenphosphate dihydrate | 0.18 mg |
| Sodium chloride | 2.73 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 3

| | |
|---|---|
| UTM0 | 25 mg titer |
| L-arginine hydrochloride | 200 mg |
| Polysorbate 80 | 10 mg |
| Disodium hydrogenphosphate dodecahydrate | 0.77 mg |
| Sodium dihydrogenphosphate dihydrate | 0.18 mg |
| Sodium chloride | 2.73 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 4

| | |
|---|---|
| UTM0 | 25 mg titer |
| L-arginine hydrochloride | 200 mg |
| Pluronic F68 | 10 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 5

| | |
|---|---|
| UTM0 | 50 mg titer |
| Maltose | 100 mg |
| Purified gelatin | 100 mg |
| Disodium hydrogenphosphate dodecahydrate | 23.2 mg |
| Sodium dihydrogenphosphate dihydrate | 5.5 mg |
| Sodium chloride | 81.8 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 6

A lyophilized soluble thrombomodulin-containing composition was prepared by using the same ingredients as Example 5. In the meanwhile, 0.1% aqueous solution of Polysorbate 80 was aseptically prepared, and the solution was dispensed in ampoules in 1.0 ml portions, and the ampoules were melt-sealed to prepare the ampoules having the solution for dissolution filled therein.

Example 7

| | |
|---|---|
| UTM0 | 25 mg titer |
| Sucrose | 100 mg |
| Purified gelatin | 100 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 8

A lyophilized soluble thrombomodulin-containing composition was prepared by using the same ingredients as Example 7. In the meanwhile, 0.1% aqueous solution of Polysorbate 80 was aseptically prepared, and the solution was dispensed in ampoules in 1.0 ml portions, and the ampoules were melt-sealed to prepare the ampoules having the solution for dissolution filled therein.

Example 9

| | |
|---|---|
| UTM1 | 25 mg titer |
| Lactose | 800 mg |
| Purified gelatin | 100 mg |
| Disodiuin hydrogenphosphate dodecahydrate | 23.2 mg |
| Sodium dihydrogenphosphate dihydrate | 5.5 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 10

| | |
|---|---|
| UTM2 | 50 mg titer |
| L-arginine hydrochloride | 200 mg |
| Purified gelatin | 100 mg |

Example 11

| | |
|---|---|
| UTM1 | 10 mg titer |
| Sucrose | 100 mg |
| Polysorbate 80 | 50 mg |
| Disodium hydrogenphosphate dodecahydrate | 23.2 mg |
| Sodium dihydrogenphosphate dihydrate | 5.5 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 12

| | |
|---|---|
| UTM2 | 50 mg titer |
| L-arginine hydrochloride | 200 mg |
| Purified gelatin | 100 mg |
| Polysorbate 80 | 10 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 13

| | |
|---|---|
| RTM1 | 25 mg titer |
| Lactose | 200 mg |
| Polysorbate 80 | 10 mg |
| Disodium hydrogenphosphate dodecahydrate | 0.77 mg |
| Sodium dihydrogenphosphate dihydrate | 0.18 mg |
| Sodium chloride | 81.8 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 14

| | |
|---|---|
| RTM1 | 25 mg titer |
| Lactose | 200 mg |
| Pluronic F68 | 10 mg |
| Disodium hydrogenphosphate dodecahydrate | 0.77 mg |
| Sodium dihydrogenphosphate dihydrate | 0.18 mg |
| Sodium chloride | 81.8 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 15

| | |
|---|---|
| RTM2 | 25 mg titer |
| Lactose | 100 mg |
| Purified gelatin | 100 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 16

A lyophilized soluble thrombomodulin-containing composition was prepared by using the same ingredients as Example 15. In the meanwhile, 0.1% aqueous solution of Polysorbate 80 was aseptically prepared, and the solution was dispensed in ampoules in 1.0 ml portions, and the ampoules were melt-sealed to prepare the ampoules having the solution for dissolution filled therein.

Example 17

| | |
|---|---|
| RTM2 | 10 mg titer |
| Maltose | 100 mg |
| Purified gelatin | 100 mg |
| Disodium hydrogenphosphate dodecahydrate | 0.77 mg |
| Sodium dihydrogenphosphate dihydrate | 0.18 mg |
| Sodium chloride | 81.8 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 18

| | |
|---|---|
| RTM2 | 10 mg titer |
| Maltose | 100 mg |
| Purified gelatin | 100 mg |
| Pluronic F68 | 10 mg |
| Disodium hydrogenphosphate dodecahydrate | 0.77 mg |
| Sodium dihydrogenphosphate dihydrate | 0.18 mg |
| Sodium chloride | 81.8 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 19

| | |
|---|---|
| UTM0 | 25 mg titer |
| L-arginine hydrochloride | 100 mg |
| Lactose | 100 mg |
| Polysorbate 80 | 10 mg |
| Disodium hydrogenphosphate dodecahydrate | 0.77 mg |
| Sodium dihydrogenphosphate dihydrate | 0.18 mg |
| Sodium chloride | 2.73 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 20

| | |
|---|---|
| UTM0 | 25 mg titer |
| L-arginine hydrochloride | 100 mg |
| Maltose | 100 mg |
| Pluronic F68 | 10 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

Example 21

| | |
|---|---|
| UTM1 | 10 mg titer |
| Lactose | 100 mg |
| Sucrose | 100 mg |
| Polysorbate 80 | 50 mg |
| Disodium hydrogenphosphate dodecahydrate | 23.2 mg |
| Sodium dihydrogenphosphate dihydrate | 5.5 mg |

The ingredients were dissolved in distilled water for injections to make up a total volume of 10 ml, and the resulting solution was aseptically filtered. The filtrate was filled in sterilized vials in 1.0 ml portions, and the content of the vials was lyophilized to prepare the lyophilized soluble thrombomodulin-containing composition.

SEQUENCE LISTING

Sequence ID NO.: 1
Sequence length: 28
Sequence type: amino acid
Molecule type: protein
Source organism: human
Sequence: Ala—Pro—Ala—Glu—Pro—Gln—Pro—Gly—
1                                       5
Gly—Ser—Gln—Cys—Val—Glu—His—Asp—
10                                      15
Cys—Phe—Ala—Leu—Tyr—Pro—Gly—Pro—
20
Ala—Thr—Phe—Leu—
25

Industrial Utility

As described above, the soluble thrombomodulin-containing composition of the present invention is stable throughout the processes of freezing, drying, storage, temperature elevation, and dissolution. In particular, the lyophilized soluble thrombomodulin-containing composition of the present invention has an excellent long term storability at room temperature. The critical components for the stabilization or the anti-adsorption that have been found in the present invention are highly safe, and when the composition of the present invention is used for a medicament, such additives enable the high quality of the medicament to be retained for a prolonged period with no risk of inactivation or aggregate formation. In particular, the lyophilized soluble thrombomodulin-containing composition of the present invention is sufficiently stable to endure the storage at 50° C. for 6 months. In addition, the soluble thrombomodulin-containing composition of the present invention would not exhibit adsorption of the soluble thrombomodulin even when it is diluted to constitute an aqueous solution of a low concentration, and therefore, it can be diluted with an infusion before its administration at clinical sites without undergoing any decrease in the effective amount of the soluble thrombomodulin. Therefore, the soluble thrombomodulin-containing composition of the present invention would constitute a highly safe, room temperature-storable prophylactic or therapeutic agent that can be used for blood coagulation disorder-related diseases. The soluble thrombomodulin-containing composition of the present invention would also constitute a prophylactic or therapeutic agent for blood coagulation disorder-related diseases which would not exhibit adsorption of the soluble thrombomodulin onto the container surface upon clinical use. The soluble thrombomodulin-containing composition, the production method therefor, the stabilization agent, the stabilization method, the anti-adsorption agent, and the anti-adsorption method of the present invention may also be utilized in the purification of the soluble thrombomodulin, and in the storage of soluble thrombomodulin stock.

We claim:

1. A stable soluble thrombomodulin-containing composition wherein said composition comprises
   a soluble thrombomodulin, and
   at least one member selected from the group consisting of maltose, lactose, sucrose, arginine and a salt of arginine.

2. A stable soluble thrombomodulin-containing composition wherein said composition comprises
   a soluble thrombomodulin,
   at least one member selected from the group consisting of maltose, lactose, sucrose, arginine and a salt of arginine, and
   a nonionic surface-active agent.

3. The stable soluble thrombomodulin-containing composition according to any one of claims 1 wherein said soluble thrombomodulin is a human urine soluble thrombomodulin.

4. The stable soluble thrombomodulin-containing composition according to claim 3 wherein said human urine soluble thrombomodulin is a substance having properties as described below:
   a) molecular weight: 72,000±3,000
      (measured by sodium dodecyl sulfate (SDS)-polyacrylamide gel electrophoresis (PAGE) under non-reduced condition);
   b) isoelectric point: 3.9±0.2;
   c) terminal amino acid sequence;
      N terminal: Ala-Pro-Ala-Glu-Pro-Gln-Pro-Gly-Gly-Ser-Gln-Cys-Val-Glu-His-Asp-Cys-Phe-Ala-Leu-Tyr-Pro-Gly-Pro-Ala-Thr-Phe-Leu- (SEQ ID NO:1), and
      C terminal: -Leu-Ala-Arg or -Leu-Val-Arg; and
   d) sugar composition (% by weight):
      neutral sugar: 5.5±1.0%
         (measured by phenol sulphuric acid method),
      amino sugar: 2.2±1.0%
         (measured by Elson-Morgan's method (Blix's modification)), and
      sialic acid: 2.8±1.5%
         (measured by Warren's method).

5. The stable soluble thrombomodulin-containing composition according to claim 3 wherein said human urine soluble thrombomodulin is a substance having properties as described below:
   a) molecular weight: 79,000±3,000
      (measured by SDS-PAGE under non-reduced condition);
   b) isoelectric point: 3.8±0.2;
   c) terminal amino acid sequence:
      N terminal: Ala-Pro-Ala-Glu-Pro-Gln-Pro-Gly-Gly-Ser-Gln-Cys-Val-Glu-His-Asp-Cys-Phe-Ala-Leu-Tyr-Pro-Gly-Pro-Ala-Thr-Phe-Leu- (SEQ ID NO:1), and
      C terminal: -Leu-Ala-Arg or -Leu-Val-Arg; and
   d) sugar composition (% by weight):
      neutral sugar: 6.2±1.0%
         (measured by phenol sulphuric acid method),
      amino sugar: 3.1±1.0%
         (measured by Elson-Morgan's method (Blix's modification)), and
      sialic acid: 3.8±1.5%
         (measured by Warren's method).

6. The stable soluble thrombomodulin-containing composition according to any one of claims 1 wherein said soluble thrombomodulin is a recombinant human soluble thrombomodulin.

7. A stable soluble thrombomodulin-containing composition wherein said composition comprises
   two or more molecular species of soluble thrombomodulins, and
   at least one member selected from the group consisting of maltose, lactose, sucrose, arginine and a salt of arginine.

8. A stable soluble thrombomodulin-containing composition wherein said composition comprises
   two or more molecular species of soluble thrombomodulins,
   at least one member selected from the group consisting of maltose, lactose, sucrose, arginine and a salt of arginine, and
   a nonionic surface-active agent.

9. The stable soluble thrombomodulin-containing composition according to any one of claims 1, 7 or 8 wherein said composition has been lyophilized.

10. A method for producing the stable soluble thrombomodulin-containing composition according to any one of claims 1 comprising the step of preparing a solution of at least one species of soluble thrombomodulin, and at least one member selected from the group consisting of maltose, lactose, sucrose, arginine and a salt of arginine; and a nonionic surface-active agent.

11. A method for producing the stable soluble thrombomodulin-containing composition according to claim 10 comprising the step of lyophilizing the soluble thrombomodulin-containing composition in the form of the solution of at least one species of soluble thrombomodulin, and at least one member selected from the group consisting of maltose, lactose, sucrose, arginine and a salt of arginine.

12. A method for stabilizing a soluble thrombomodulin wherein said method comprises the step of adding at least one member selected from the group consisting of maltose, lactose, sucrose, arginine and a salt of arginine to the soluble thrombomodulin.

13. The method of claim 1 wherein the amount of said member used is 0.1–1000 mg per 1 mg titer of soluble thrombomodulin.

14. The method of claim 1 wherein the amount of sucrose is 0.5 to 50 mg per 1 mg titer of soluble thrombomodulin.

* * * * *

UNITED STATES PATENT AND TRADEMARK OFFICE
CERTIFICATE OF CORRECTION

PATENT NO. : 5,834,028
DATED : November 10, 1998
INVENTOR(S) : Yasuyuki KUNUHIRO et al.

It is certified that error appears in the above-identified patent and that said Letters Patent is hereby corrected as shown below:

In Claims:

<u>Claim 3</u>
Line 2, change "claims 1" to --claims 1 or 2--.

<u>Claim 6</u>
Line 2, change "claims 1" to --claims 1 or 2--.

<u>Claim 9</u>
Line 2, change "claims 1, 7 or 8" to --claims 1, 2, 7 or 8--.

<u>Claim 10</u>
Line 3, change "claims 1" to --claims 1 and 2--.

Signed and Sealed this

Twenty-third Day of May, 2000

Attest:

Q. TODD DICKINSON

*Attesting Officer*    *Director of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:

(A) LENGTH: 28 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:1:

```
Ala Pro Ala Glu Pro Gln Pro Gly Gly Ser Gln Cys Val Glu His Asp
 1               5                      10                     15

Cys Phe Ala Leu Tyr Pro Gly Pro Ala Thr Phe Leu
                 20                  25
```